United States Patent [19]

Schober et al.

[11] Patent Number: 4,654,058

[45] Date of Patent: Mar. 31, 1987

[54] DEVICE FOR SAMPLING PARTICLES FROM THE EXHAUST GASES OF A SELF-IGNITING INTERNAL COMBUSTION ENGINE

[75] Inventors: Karl Schober, Weinstadt; Fritz Groll, Fellbach, both of Fed. Rep. of Germany

[73] Assignee: Daimler-Benz Aktiengesellschaft, Fed. Rep. of Germany

[21] Appl. No.: 737,211

[22] Filed: May 23, 1985

[30] Foreign Application Priority Data

May 24, 1984 [DE] Fed. Rep. of Germany ....... 3419354

[51] Int. Cl.$^4$ .............................................. B01D 46/00
[52] U.S. Cl. ...................................... 55/217; 55/270; 55/357; 55/481; 55/484; 55/DIG. 30; 73/863.23; 73/863.01
[58] Field of Search ................... 55/210, 314, 270, 312, 55/478–481, 484, 357, 485, DIG. 30; 60/311; 73/28, 116, 863.23, 863.01; 210/447

[56] References Cited

U.S. PATENT DOCUMENTS

| | | | |
|---|---|---|---|
| 4,028,248 | 6/1977 | Murauskas | 210/447 |
| 4,081,255 | 3/1978 | Evans | 55/481 |
| 4,155,247 | 5/1979 | Kaczmarek et al. | 55/270 |
| 4,197,098 | 4/1980 | Stiehl et al. | 55/270 |
| 4,281,512 | 8/1981 | Mills | 55/523 |

FOREIGN PATENT DOCUMENTS 2097283 11/1982 United Kingdom ......... 55/DIG. 30

OTHER PUBLICATIONS

SAE Paper 77 08 18, 1977, pp. 207–225, "Emissions from Diesel Versions of Production Passenger Cars"; published by Society of Automotive Engineers, Inc.; 400 Commonwealth Drive, Warrendale, PA 15096.

Primary Examiner—Bernard Nozick
Attorney, Agent, or Firm—Barnes & Thornburg

[57] ABSTRACT

A compact device is provided for sampling particles from the exhaust gases of an internal combustion engine for an automotive vehicle. The device includes a dilution tunnel, to which is supplied all the exhaust gases of the internal combustion engine. From the dilution tunnel, by way of an exhaust gas distributor, a sample stream of exhaust gas is distributed to filter cylinders arranged in exhaust gas conduits in dependence on the operation of the internal combustion engine. Filter units, traversed by the sample stream of exhaust gas, are removably disposed in the filter cylinders which are vertically arranged and exhibit a filter mounting element accommodating the filter units. This filter mounting element is adapted to be swung out laterally from the filter cylinders after opening of a locking device. A plurality of filter cylinders are provided, each being associated with a specific operating phase of the internal combustion engine, and being utilized for determination of the quantity of emitted particles. A filter cylinder designed as a static cylinder is also provided. Upstream and downstream of each filter cylinder, valves are arranged which are adapted to control the flow of exhaust gas through the individual cylinders.

33 Claims, 4 Drawing Figures

DEVICE FOR SAMPLING PARTICLES FROM THE EXHAUST GASES OF A SELF-IGNITING INTERNAL COMBUSTION ENGINE

BACKGROUND AND SUMMARY OF THE INVENTION

The invention relates generally to a device for sampling particles from the exhaust gases of a self-igniting internal combustion engine and more particularly to such a device wherein a plurality of test cylinders are employed.

The literature reference "SAE Paper No. 77 08 18, 1977, pages 207-225" discloses a device of the general type for taking samples of particles from the exhaust gases of a self-igniting internal combustion engine for an automotive vehicle drive onto a roller-type test stand. The exhaust gases enter into a distributor arranged vertically on the dilution tunnel and flow therefrom through exhaust gas conduits to the filter cylinders. The exhaust gas conduits and the filter cylinders are disposed to emanate in stellar arrangement from the distributor. Consequently, the installation occupies a relatively large space. The filter units are removed from the horizontally disposed filter cylinders in an axial direction. This arrangement requires, in this direction, additional space on all sides for the mounting and dismounting, respectively, of the filter cylinders. This literature reference fails to disclose any information regarding the type of control provided for the individual filter cylinders.

It is one object of the present invention to provide a sampling device of the general type described above which has a compact size.

It is another object of the present invention to provide a sampling device which requires only a small amount of space for changing the filter units.

It is still another object of the present invention to provide a sampling device which allows optimum control of filter units disposed in the device.

These and other objects of the present invention are achieved by the provision of a compact device for sampling particles from the exhaust gases of an internal combustion engine for an automotive vehicle. This device includes a dilution tunnel, to which is supplied all the exhaust gases of the internal combustion engine. From the dilution tunnel, by way of an exhaust gas distributor, a sample stream of exhaust gas is distributed to filter cylinders arranged in exhaust gas conduits, in dependence on the operation of the internal combustion engine. Filter units, traversed by the sample stream of exhaust gas, are removably disposed in the filter cylinders which are vertically arranged and exhibit a filter mounting element accommodating the filter units. This filter mounting element is adapted to be swung out laterally from the filter cylinders after opening of a locking device. A plurality of filter cylinders are provided, each being associated with a specific operating phase of the internal combustion engine, and utilized for determination of the quantity of emitted particles. A filter cylinder designed as a static cylinder is also provided. Upstream and downstream of each filter cylinder, valves are arranged which are adapted to control the flow of the exhaust gas through the individual cylinders.

In the device of the present invention as described above, particle sampling is advantageously possible while the sample stream of exhaust gas flows continuously through the device. Due to the vertically disposed arrangement of the filter cylinders and the design enabling the swinging out of the central filter mounting elements laterally, changing of the filter units can be effected in an extremely small space. Due to the spatial orientation of the exhaust gas distributor and the nonreturn valves with respect to the filter cylinders, the device occupies a minimal amount of space.

Other objects, advantages and novel features of the present invention will become apparent from the following detailed description of the invention when considered in conjunction with the accompanying drawings.

DETAILED DESCRIPTION OF THE DRAWINGS

Figure 1:
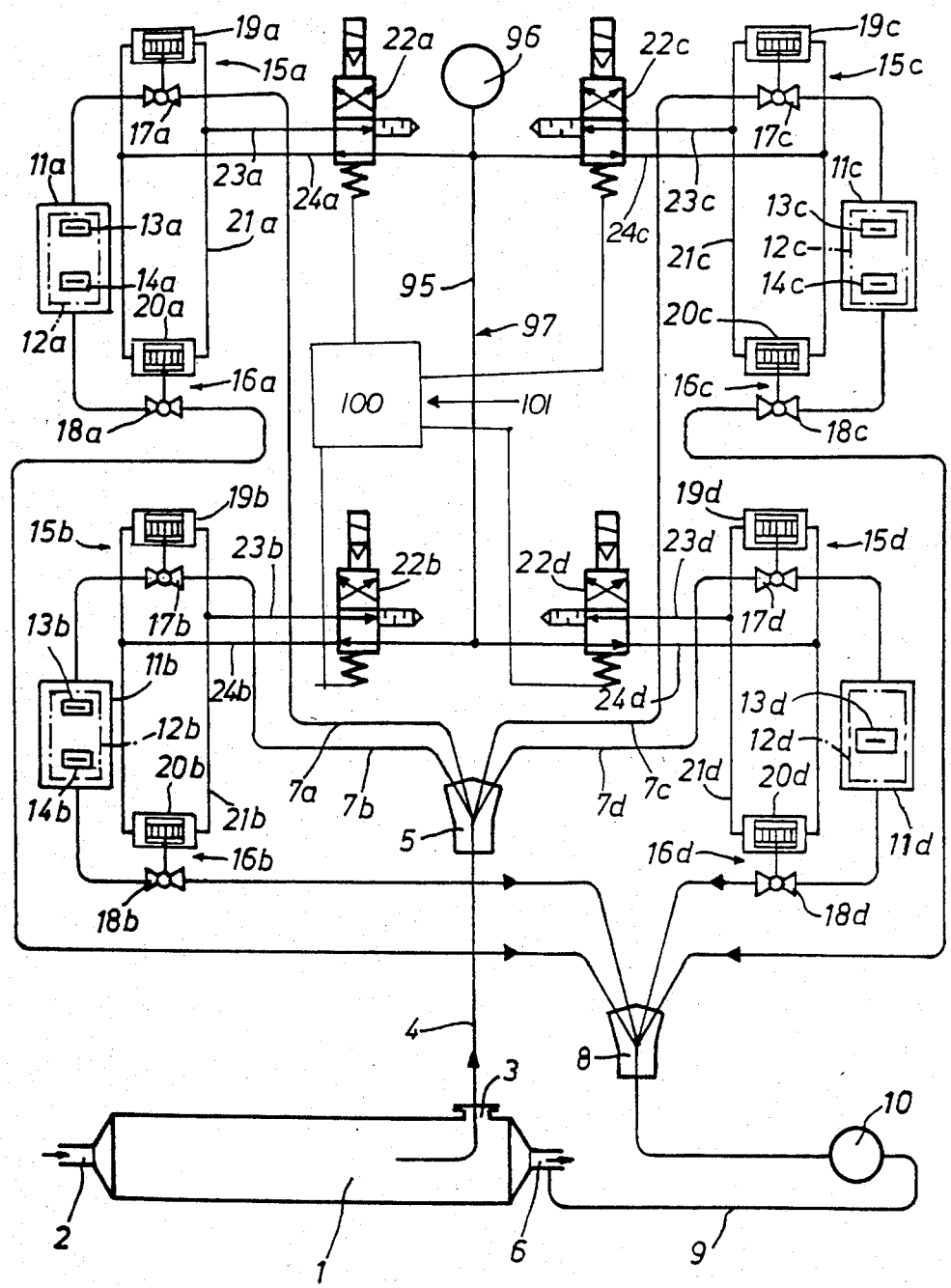
FIG. 1 shows the device of the present invention in a schematic view.

In FIG. 1, a dilution tunnel is denoted by 1. The exhaust of a self-igniting internal combustion engine of an automotive vehicle driven onto a roller-type test stand is fed to this tunnel by way of an inlet opening 2. A sample stream of exhaust gas, controlled by a volume regulator (not shown) is introduced through an outlet opening 3 and an exhaust gas conduit 4 into an exhaust gas distributor 5. The remainder of the exhaust is exhausted into the atmosphere by way of outlet opening 6. The sample stream of exhaust gas is fed from exhaust gas distributor 5 selectively to exhaust gas conduits 7a, 7b, 7c, or 7d, which terminate in exhaust gas collector manifold 8. From this collector manifold, the sample stream of exhaust gas is conducted through an exhaust gas conduit 9, wherein a vacuum pump 10 is arranged, to the outlet opening 6. From there, the sample is exhausted into the atmosphere.

Filter cylinder 11a is arranged in exhaust gas conduit 7a, filter cylinder 11b is arranged in exhaust gas conduit 7b, filter cylinder 11c is arranged in exhaust gas conduit 7c, and filter cylinder 11d is arranged in exhaust gas conduit 7d. The filter cylinder 11a comprises a filter holder 12a with two filter units 13a and 14a arranged in series in the direction of flow of the exhaust gas. The filter cylinder 11b comprises a filter holder 12b with two filter units 13b and 14b series-arranged in the exhaust gas flow direction. In a similar manner, the filter cylinder 11c comprises a filter holder 12c with two filter units 13c and 14c disposed in series in the exhaust gas flow direction. The filter cylinder 11d comprises a filter holder 12d with a filter unit 13d.

The exhaust gas conduit 7a can be closed downstream and upstream of the filter cylinder 11a by nonreturn valves 15a and 16a respectively. In like manner, the exhaust gas conduit 7b can be closed by nonreturn valves 15b and 16b respectively, and the exhaust gas conduits 7c and 7d can be closed by nonreturn valves 15c, 16c and 15d, 16d respectively. The nonreturn valves 15a –15d and 16a–16d are, in the illustrated embodiment, pneumatically operated ball valves 17a–17d and 18a-18d, located in the corresponding exhaust gas conduits 7a-7d. The pneumatic drive means 19a and 20a are arranged in a pneumatic control circuit 21a, the pneumatic drive means 19b and 20b thereof are located in a pneumatic control circuit 21b, the pneumatic drive means 19c and 20c thereof are arranged in a pneumatic control circuit 21c, and the pneumatic drive means 19d and 20d are disposed in a pneumatic control circuit 21d.

The control circuit 21a is operable by an electromagnetic IV/II-way valve 22a via pneumatic control lines 23a and 24a, control circuit 21b is operable by an electromagnetic IV/II-way valve 22b via pneumatic control lines 23b and 24b, control circuit 21c is operable by an electromagnetic IV/II-way valve 22c via pneumatic control lines 23c and 24c, and control circuit 21d is operable by an electromagnetic IV/II-way valve 22d via pneumatic control lines 23d and 24d. The control lines 24a-24d are connected to a pneumatic main control line 95 fed by a source 96 of compressed air. The pneumatic control circuits and the pneumatic control lines together form a combined pneumatic control circuit 97 for the pneumatic drive means of the ball valves. The electro-magnetic IV/II-way valves 22a-22d are regulated by means of a program entered into a programmable control device 100 which may be responsive (for example) to an external engine parameter or exhaust parameter 101 or a time sequence.

After starting the self-igniting internal combustion engine, with an exhaust gas temperature of below 52° C., the IV/II-way valves 22a-22d are in the illustrated position. The compressed air generated by the compressed-air source 96 causes, via the main control line 95, control lines 24a-24d, and control circuits 21a-21d, the pneumatic drive means 19a-19d and 20a-20d, to close the ball valves 17a-17d and 18a-18d. In this position, none of the filter cylinders 11a-11d is exposed to the flow of exhaust gases. Rather, exhaust gases flowing through the inlet opening 2 into the dilution tunnel 1 are exhausted into the atmosphere via the outlet opening 6. After flowing through the pneumatic drive means 19a-19d, the compressed air is likewise exhausted into the atmosphere via the control lines 23a-23d and the IV/II-way valves 22a-22d.

Once the exhaust gases reach a temperature of 52° C., the preset program switches the IV/II-way valve 22a, and the compressed air causes the pneumatic drive means 19a and 20a, by way of the control line 23a and the control circuit 21a, to open the ball valves 17a and 18a. On account of the vacuum produced by the vacuum pump 10, a partial quantity of exhaust gas from the dilution tunnel 1 is introduced into the exhaust gas distributor 5 and flows through the exhaust gas conduit 7a through the ball valve 17a arranged therein, through the filter cylinder 11a comprising a test filter cylinder, and through the ball valve 18a to the exhaust gas collector manifold 8. From the distributor, the sample stream of exhaust gas is passed through the exhaust gas conduit 9 to the outlet opening 6 of the dilution tunnel 1. From the outlet opening 6, this sample stream of exhaust gas is exhausted into the atmosphere together with the other exhaust gases.

In this operating phase of the internal combustion engine, the IV/II-way valve 22a is operated by a program, for example, in such a way that the filter cylinder 11a is traversed by the sample stream of exhaust gas for a time period of 505 seconds. During this step, the particles contained in the exhaust gases, e.g., soot, are deposited on the filter unit 13a. After elapse of the 505 seconds, the IV/II-way valve 22a is switched back into the indicated starting position and, at the same time, the IV/II-way valve 22d is operated. Thereby, on the one hand, the ball valves 17a and 18a are closed again and, on the other hand, the ball valves 17d and 18d are opened due to the action of compressed air on the pneumatic drive means 19d and 20d via the control line 23d and the control circuit 21d.

The sample stream of exhaust gas now flows from the exhaust gas distributor 5 through the exhaust gas conduit 7d, through the ball valve 17d arranged therein, through the filter cylinder 11d comprising a static filter cylinder, and through the ball valve 18d to the exhaust gas collector manifold 8. From the distributor the sample stream of exhaust gas is passed through the exhaust gas conduit 9 to the outlet opening 6 of the dilution tunnel 1 from where it is exhausted into the atmosphere together with the other exhaust gases. The way in which the filter units are removed from the individual filter cylinders to analyze the particles is described later with reference to FIGS. 2-4. The IV/II-way valve 22d is operated by the program, for example, in such a way that the sample stream of exhaust gas is passed through the filter cylinder 11d for a time period of 600 seconds. During this step, the particles contained in the exhaust gases are deposited on the filter unit 13d, but these particles are not utilized for analysis. This filter unit 13d is arranged in the filter cylinder 11d merely for the purpose of maintenance of the vacuum. After elapse of the 600 seconds, the IV/II-way valve 22d is again switched into the illustrated starting position, and simultaneously the IV/II-way valve 22b is operated. Thereby, on the one hand, the ball valves 17d and 18d are closed and, on the other hand, the ball valves 17b and 18b are opened on account of the action of compressed air on the pneumatic drive means 19b and 20b via the control line 23b and the control circuit 21b.

The sample stream of exhaust gas now flows from the exhaust gas distributor 5 through the exhaust gas conduit 7b, through ball valve 17b arranged therein, through the filter cylinder 11b comprising a test filter cylinder, and through the ball valve 18b to the exhaust gas collector manifold 8. From the distributor, the sample stream of exhaust gas is conducted through the exhaust gas conduit 9 to the outlet opening 6 of the dilution tunnel 1 from where it is exhausted into the atmosphere together with the other exhaust gases. The IV/II-way valve 22b is operated, in this operating phase of the internal combustion engine, already stabilized with respect to the operating temperature, by means of the program, for example in such a way that the sample stream of exhaust gas is passed through the filter cylinder 11b for a time period of 867 seconds. During this step, the particles contained in the exhaust gases are deposited on the filter unit 13b. After elapse of the 867 seconds, the IV/II-way valve 22b is returned into the illustrated starting position and, at the same time, the IV/II-way valve 22d is operated. Thereby, on the one hand, the ball valves 17b and 18b are closed again and, on the other hand, the ball valves 17d and 18d are opened due to the effect of compressed air on the pneumatic drive means 19d and 20d via the control line 23d and the control circuit 21d. The sample stream of exhaust gas again flows from the exhaust gas distributor 5 through the exhaust gas conduit 7d, through the ball valve 17d arranged therein, through the filter cylinder 11d and the ball valve 18d, to the exhaust gas collector manifold 8. From the distributor, the sample stream of exhaust gas is passed through the exhaust gas conduit 9 to the outlet opening 6 of the dilution tunnel 1 from where it is exhausted into the atmosphere together with the other exhaust gases. The IV/II-way valve 22d is operated by the program, in turn, so that the filter cylinder 11d is traversed by the sample stream of exhaust gas for a time period of 600 seconds. After elapse of the 600 seconds, the IV/II-way valve 22d is switched back into the illustrated starting position, and the IV/II-way valve 22c is actuated at the same time. Thereby, on the one hand, the ball valves 17d and 18d are closed again and, on the other hand, the ball valves 17c and 18c are opened due to compressed air acting on the pneumatic drive means 19c and 20c via the control line 23c and the control circuit 21c.

The sample stream of exhaust gas now flows from the exhaust gas distributor 5 through the exhaust gas conduit 7c and through the ball valve 17c arranged therein, through the filter cylinder 11c comprising a test filter cylinder and through the ball valve 18c to the exhaust gas collector manifold 8. From the distributor, the sample stream of exhaust gas is conducted through the exhaust gas conduit 9 to the outlet opening 6 of the dilution tunnel 1 from where it is exhausted into the atmosphere together with the other exhaust gases. The IV/II-way valve 22c is activated by the program in this operating phase of the internal combustion engine which, with respect to the operating temperature, is in the transitional phase toward hot start-up, for example, in such a way that the filter cylinder 11c is traversed by the sample stream of exhaust gas for a time period of 505 seconds. During this step, the particles contained in the exhaust gases are deposited on the filter unit 13c. With this step, the program could be terminated. However, it is also possible to reintroduce the sample exhaust gas stream into the filter cylinder 11d, if desired.

Figure 2:
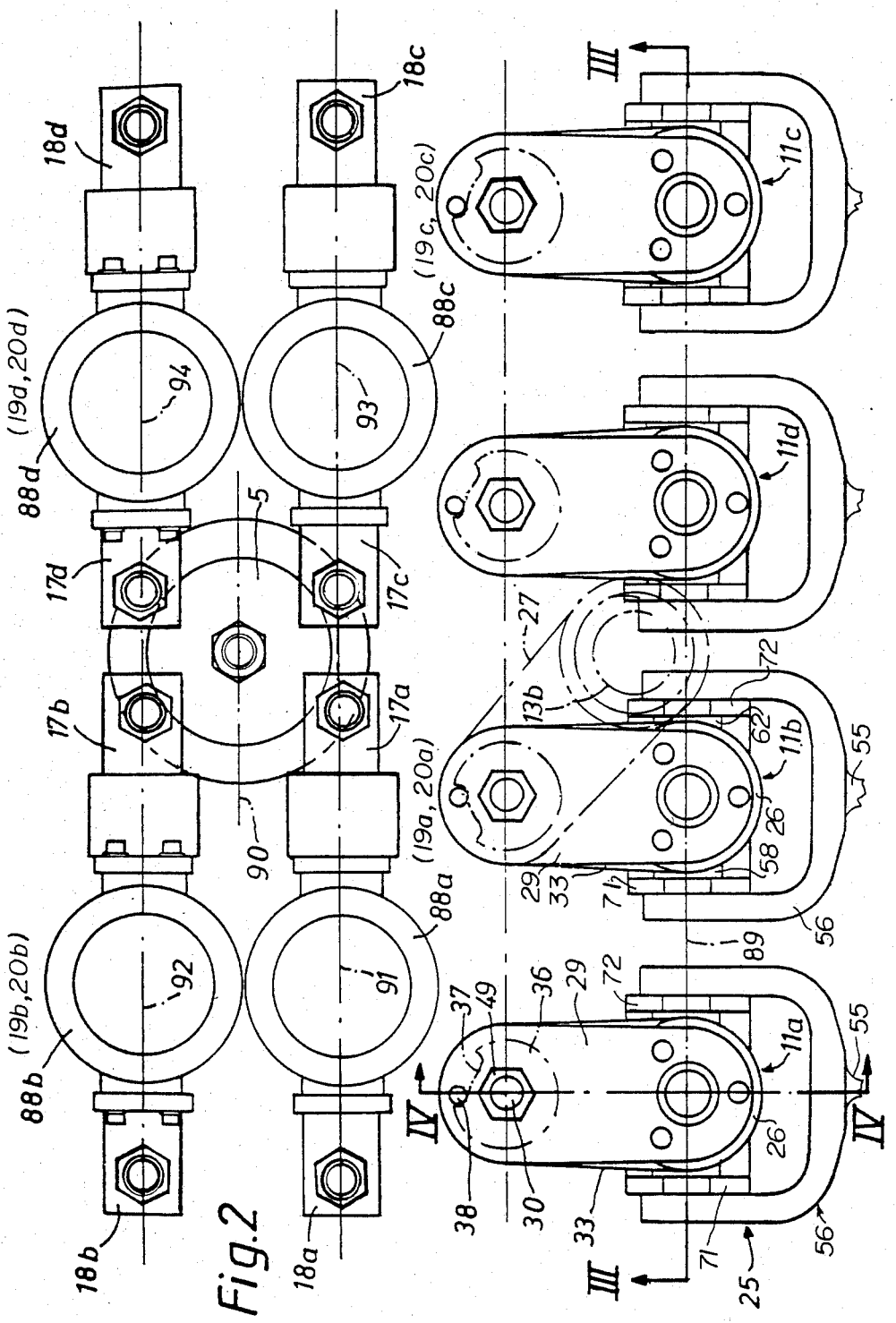
Fig. 2 is a top view of a distributor, valves, pneumatic actuator and filters of FIG. 1 without interconnection for the sake of clarity.
Figure 3:
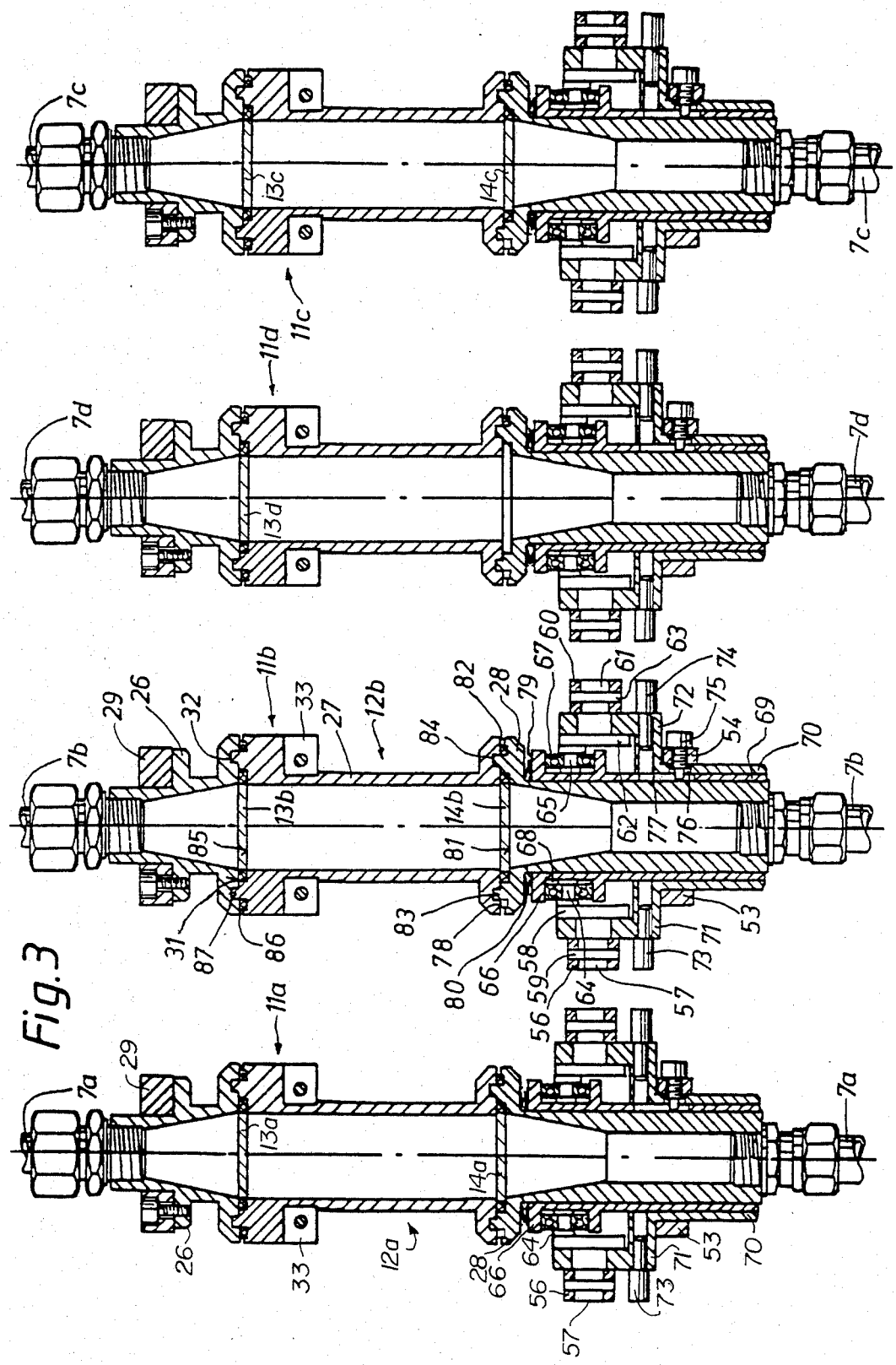
FIG. 3 is a section along line III—III of FIG. 2 with conduits.
Figure 4:
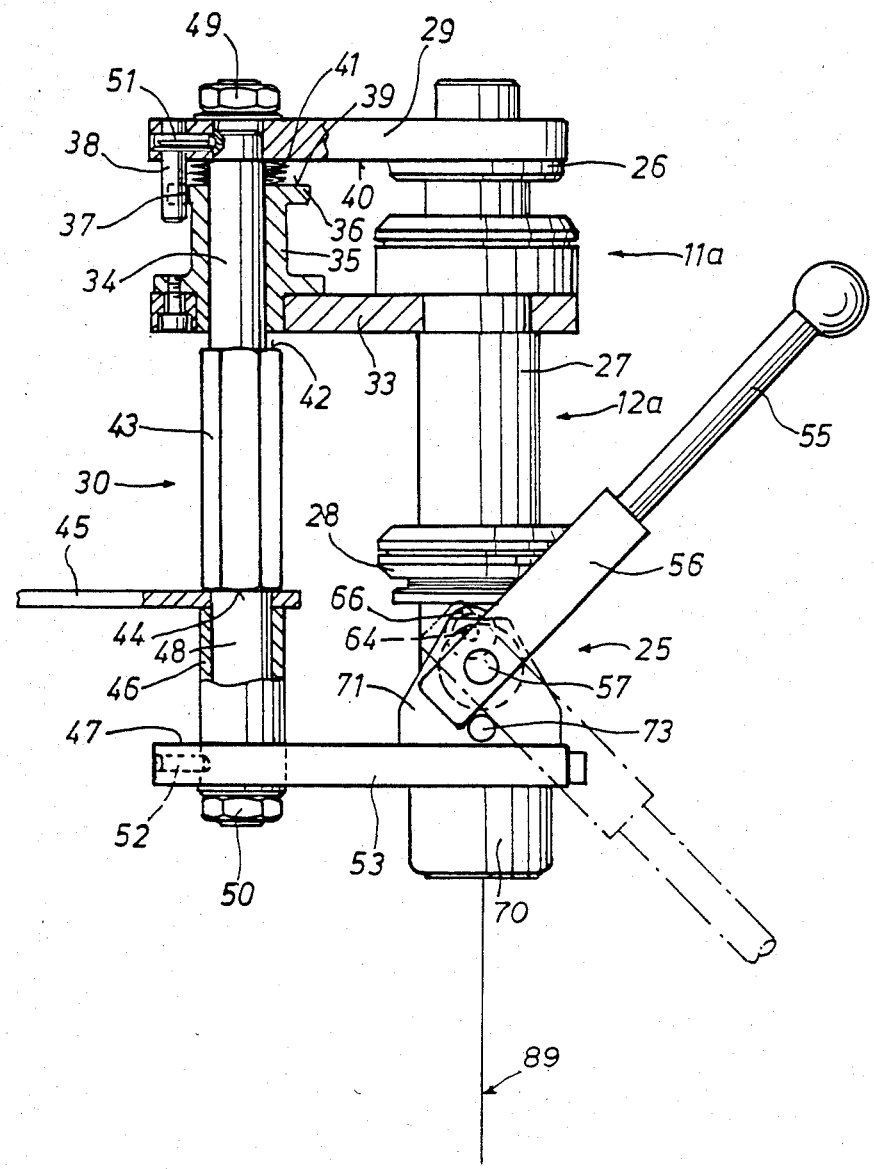
FIG. 4 is a partial sectional view along line IV—IV of FIG. 2.

FIGS. 2-4 illustrate, using the filter cylinder 11b, the structure of the filter cylinders and of the locking units 25 in detail. Referring now to FIG. 4, the filter holder 12a comprises a fixed supporting member 26, a central filter mounting element 27 and a lower filter mounting element 28. The supporting member 26 is rigidly joined to a guide shaft 30 via a bearing part 29 and exhibits an annular centering groove 32 (shown in FIG. 3) on the end face 31 facing the central filter mounting element 27. The central filter mounting element 27 is rigidly connected, by way of a supporting member 33, to a guide bushing 35 arranged rotatably on a guide section 34 of the guide shaft 30. The guide bushing 35 exhibits, at the end facing the supporting member 26, a guide collar 36 with a guide recess 37, which recess 37 cooperates with a stop pin 38 fixedly connected to the supporting member 33. Several springs 41, arranged alternatingly in their orientation, are disposed under pre-tensioning between the end face 39 of the guide collar 36 and the end face 40 of the supporting member 33. The guide bushing 35 is displaceable in the vertical direction up to the end face 42 of an abutment zone 43 of the guide shaft 30. The guide shaft 30 with the end face 44 of the abutment zone 43, rests on a fixedly disposed bearing element 45.

The bearing element 45 is arranged together with a guide bushing 46 and a bifurcate supporting element 47 on a bearing section 48 of the guide shaft 30. In the axial direction, the bearing element 29, the springs 41 and the guide bushing 35 are secured on the guide section 34 by the threaded nut 49, and the supporting element 47. The guide bushing 46 and the bearing element 45 are secured on the bearing section 48 by the threaded nut 50. The centering pin 51 rotationally connects the bearing element 29 with the guide section 34, and the centering pin 52 rotationally connects the supporting element 47 with the bearing section 48.

The locking means 25 rests on the legs 53 and 54 of the supporting element 47. The locking means 25 comprises a bifurcate operating lever 55. Referring now to FIG. 3, leg 56 is rotationally connected with eccentric pin 57 carrying eccentric disk 58 by means of a securing pin 59. The leg 60 of this lever 55 is rotationally connected with an eccentric pin 61 carrying an eccentric disk 62 by means of a securing pin 63. The eccentric disk 58 has a guide stud 64, and the eccentric disk 62 has a guide stud 65. The guide stud 64 is arranged by way of a ball bearing 66, and the guide stud 65 is arranged by way of a ball bearing 67 in a continuous guide groove 68 of a guide cylinder 69 axially displaceably mounted on the lower filter mounting element 28. A supporting cylinder 70 is guided on the guide cylinder 69 and rests with a supporting arm 71 on the leg 53 of the supporting element 47 and with a supporting arm 72 on the leg 54 of the supporting element 47. The eccentric pin 57 and a stop pin 73 are arranged in the supporting arm 71, and the eccentric stud 61 and a stop pin 74 are arranged in the supporting arm 72. A securing screw 75 is threaded into the leg 54 of the supporting element 47. This screw penetrates a mounting bore 76 of the supporting cylinder 70 and projects into a guide groove 77 of the guide cylinder 69, so that the supporting cylinder 70 and the guide cylinder 69 are secured against rotation with respect to the supporting element 47. Several alternatingly oriented springs 80 are arranged with pretensioning between an end face 78 of the lower filter mounting element 28 and an end face 79 of the guide cylinder 69.

The lower filter mounting element 28 exhibits a cylindrical recess 81 on the end face 82 facing the central filter mounting element 27, for accommodation of the filter unit 14b and a guide collar 83. The guide collar cooperates with a centering groove 84 in the central filter mounting element 27. The filter unit 13b lies in a cylindrical recess 85 in the end face 86 of the central filter mounting element 27 facing the supporting member 26, and a guide collar 87 at the end face 86 cooperates with the centering groove 32 of the supporting member 26.

In a deviation from the illustration in FIG. 1 wherein each ball valve is associated with a separate pneumatic drive means, FIG. 2 shows schematically another contemplated structure for operating the ball valves. In this arrangement, the ball valves 17a and 18a are associated with a pneumatic drive means 88a common to both of them. The ball valves 17b and 18b have a common pneumatic drive means 88b, as do the ball valves 17c and 18c (i.e., 88c) and the ball valves 17d and 18d (i.e., 88d). The pneumatic drive means 88a–88d are actuated in the same way as in the actuation of the pneumatic drive means 19a–19d and 20a–20d illustrated in FIG. 1.

The filter cylinders 11a–11d are arranged perpendicularly upright in a plane 89, and the exhaust gas distributor 5 is located in a plane 90 lying in parallel side-by-side relationship with plane 89. In an H-shaped arrangement with respect to this plane 90, the ball valves 17a and 18a are disposed along with the pneumatic drive means 88a in a plane 91. In like manner, ball valves 17b and 18b and the pneumatic drive means 88b are located in a plane 92, ball valves 17c and 18c and the pneumatic drive means 88c are disposed in a plane 93, and ball valves 17d and 18d and the pneumatic drive means 88d are arranged in a plane 94.

After the sample stream of exhaust gas has passed through the filter cylinder 11b for example, for a time period of 867 seconds, the program causes the exhaust gas conduit 7b to be closed by the ball valves 17b and 18b. In order to be able to remove the filter unit 13b from the central filter mounting element 27, the operating lever 55 is swung into the position illustrated in dot-dash lines in FIG. 4, as determined by the stop pins 73 and 74. During this process, the eccentric studs 57 and 61 are turned, and the guide cylinder 69 is shifted vertically downwardly by the guide studs 64 and 65. This downward motion is followed by the lower filter mounting element 28, the central filter mounting element 27, the supporting member 33, and the guide bushing 35, until the supporting member 33 rests on the end face 42 of the abutment zone 43 of the guide shaft 30. In this position, the guide collar 87 of the central filter mounting element 27 has moved out of the centering groove 32 of the supporting member 26.

The eccentric pins 57 and 61 are designed so that the downward movement, caused by the guide studs 64 and 65, of the guide cylinder 69, and accordingly also the downward movement of the lower filter mounting element 28, is greater than the downward motion of the central filter mounting element 27, limited by the abutment zone 43, by an amount such that when the legs 56 and 60 of the operating lever 55 contact the stop pins 73 and 74, the guide collar 83 of the lower filter mounting element 28 has also left the centering groove 84 of the central filter mounting element 27. The central filter mounting element 27 can now be swung into the position shown in dot-dash lines in FIG. 2. This position is delimited by the stop pin 38. The filter unit 13b can then be removed from the cylindrical recess 85 for the purpose of particle analysis. The filter unit 14b is likewise accessible in this position of the central filter mounting element 27 and can be examined for the presence of deposited particles. If this is the case, then the filter unit 13b is defective and accordingly the test results are inaccurate.

Although the invention has been described and illustrated in detail, it is to be clearly understood that the above is to be taken by way of illustration and example only and not by way of limitation. The spirit and scope of the invention are to be limited only by the terms of the appended claims.

What is claimed is:

1. An apparatus for testing engine exhaust, said apparatus including exhaust collecting means for collecting internal combustion engine exhaust, sampling means in fluid communication with said exhaust collecting means, and exhaust receiving means in fluid communication with said sampling means for receiving sampled exhaust, wherein said sampling means comprising:
at least one filter cylinder means being capable of accommodating at least one filter means for filtering said exhaust,
said filter cylinder means having filter mounting means for accommodating said filter means, said filter mounting means being laterally pivotable from said filter cylinder means to facilitate filter replacement.

2. An apparatus according to claim 1, wherein releasable locking means are disposed adjacent said filter mounting means for selectively preventing said filter mounting means from laterally pivoting from said filter cylinder means.

3. An apparatus according to claim 1, further comprising limiting stop pin means for limiting lateral pivoting motion of said filter mounting means.

4. An apparatus according to claim 1, wherein said at least one filter cylinder means comprises a plurality of filter cylinder means.

5. An apparatus according to claim 4, wherein said plurality of filter cylinder means are vertically disposed.

6. An apparatus according to claim 4, further comprising means for selectively communicating each of said filter cylinder mean with said exhaust collecting means.

7. An apparatus according to claim 6, wherein said means for selectively communicating each said filter cylinder with said exhaust collecting means comprises non-return valve means upstream and downstream of each said filter cylinder means.

8. An apparatus according to claim 7, further comprising control means for selectively opening and closing said non-return valve means.

9. An apparatus according to claim 7, wherein said non-return valve means comprises pneumatically operated ball valve means.

10. An apparatus according to claim 8, wherein said control means is responsive to a temperature of said engine exhaust.

11. An apparatus according to claim 8, wherein said control means selectively communicates one said filter cylinder means with said exhaust collecting means during one of a series of preselected engine operating phases.

12. An apparatus according to claim 11, further comprising static cylinder means, said control means being capable of selectively communicating said static cylinder means with said exhaust collecting means when said engine is in a non-preselected engine operating phase.

13. An apparatus according to claim 12, wherein said one said filter cylinder means accommodates two said filter means and said static cylinder means accommodates one said filter means.

14. An apparatus according to claim 12, wherein said static cylinder means includes filter holder means comprising static cylinder stationary supporting means and static cylinder filter mounting means accommodating static cylinder filter means.

15. An apparatus according to claim 11, wherein said exhaust collecting means includes exhaust gas collector manifold means, said filter cylinder means being vertically oriented in a row, said exhaust gas collector manifold means being positioned adjacent said row in side-by-side relationship to said row.

16. An apparatus according to claim 15, wherein said non-return valve means and said pneumatic drive means associated with said non-return valve means are disposed adjacent said exhaust gas collector manifold means.

17. An apparatus according to claim 16, wherein said non-return valve means and said pneumatic drive means associated with said non-return valve means are disposed in rows adjacent said exhaust gas collector manifold means.

18. An apparatus according to claim 8, wherein said control means comprises electromagnetic valve means.

19. An apparatus according to claim 8, wherein said control means comprises pneumatic drive means.

20. An apparatus according to claim 8, wherein said control means comprises programmable control means.

21. An apparatus according to claim 1, wherein said filter cylinder means includes stationary supporting means adjacent said filter mounting means.

22. An apparatus according to claim 21, wherein said filter cylinder means includes lower filter mounting means for accommodating said filter means.

23. An apparatus according to claim 22, further comprising guide shaft means, said stationary supporting means being fixedly connected to said guide shaft means, said filter mounting means being attached to said guide shaft means, said filter mounting means being axially and pivotally displaceable relative to said guide shaft means, and said lower filter mounting means being attached to said guide shaft means, said lower filter mounting means being axially displaceable relative to said guide shaft means.

24. An apparatus according to claim 23, further comprising releasible locking means disposed adjacent said filter mounting means for selectively preventing said filter mounting means from laterally pivoting from said filter cylinder means, said stationary supporting means, said filter mounting means and said lower filter mounting means being axially aligned, said supporting means contacting said filter mounting means, said lower filter mounting means contacting said filter mounting means when said locking means is in a closed position.

25. An apparatus according to claim 24, wherein said filter mounting means is axially displaced relative to said supporting means and said lower filter mounting means is axially displaced relative to said filter mounting means when said locking means is in an open position, thereby permitting lateral pivoting of said filter mounting means about said guide shaft means.

26. An apparatus according to claim 25, wherein said supporting means and said lower filter mounting means each have centering means and said filter mounting means has complimentary centering means for engaging said supporting means and said lower filter mounting means.

27. An apparatus according to claim 25, wherein said guide shaft means has abutment means for limiting said axial displacement of said filter mounting means.

28. An apparatus according to claim 27, wherein said guide shaft means includes stop pin means, said stop pin means limiting movement of said locking means.

29. An apparatus according to claim 28, said locking means comprises operating lever means rotatably mounted on said lower filter mounting means, rotation of said operating lever means being limited by said stop pin means.

30. An apparatus according to claim 4, wherein said exhaust collecting means includes exhaust gas collector manifold means, said filter cylinder means being vertically oriented in a row, said exhaust gas collector manifold means being positioned adjacent said row in side-by-side relationship to said row.

31. An apparatus according to claim 30, wherein said plurality of filter cylinder means comprises three filter cylinder means.

32. An apparatus according to claim 1, wherein said filter cylinder means is capable of accommodating two said filter means.

33. An apparatus according to claim 32, wherein two said filter means are arranged in series.

* * * * *